United States Patent [19]

Tsunekawa et al.

[11] Patent Number: 4,783,491

[45] Date of Patent: Nov. 8, 1988

[54] DENTAL MATERIALS HAVING X-RAY CONTRASTABILITY

[75] Inventors: Masayoshi Tsunekawa, Toyonaka; Masaya Ishibashi, Yao, both of Japan

[73] Assignee: Sankin Kogyo Kabushiki Kaisha, Osaka, Japan

[21] Appl. No.: 756,974

[22] PCT Filed: Dec. 12, 1984

[86] PCT No.: PCT/JP84/00587

§ 371 Date: Jun. 26, 1985

§ 102(e) Date: Jun. 26, 1985

[87] PCT Pub. No.: WO86/03404

PCT Pub. Date: Jun. 19, 1986

[51] Int. Cl.$^4$ .......................... A61K 6/08; A61C 8/00
[52] U.S. Cl. .................... 523/117; 433/201.1; 433/228.1; 433/199.1; 522/77; 523/116
[58] Field of Search ................. 523/116, 117; 433/201.1, 228.1

[56] References Cited

U.S. PATENT DOCUMENTS

| | | | |
|---|---|---|---|
| 3,345,401 | 10/1967 | May | 526/313 |
| 3,715,331 | 2/1973 | Molnar | 523/120 |
| 3,932,181 | 1/1976 | Ray-Chaudhuri | 526/296 |
| 4,302,376 | 11/1981 | Walkowiak et al. | 106/35 |
| 4,442,239 | 4/1984 | Tsunekawa et al. | 523/116 |
| 4,499,251 | 2/1985 | Omura et al. | 523/116 |
| 4,515,930 | 5/1985 | Omura et al. | 523/116 |
| 4,525,493 | 6/1985 | Omura et al. | 523/116 |
| 4,537,940 | 8/1985 | Omura et al. | 523/116 |
| 4,539,382 | 9/1985 | Omura et al. | 523/116 |
| 4,696,955 | 9/1987 | Kuhlmann | 522/77 |

FOREIGN PATENT DOCUMENTS

| | | |
|---|---|---|
| 142921 | 5/1985 | European Pat. Off. |
| 3342601 | 3/1985 | Fed. Rep. of Germany |
| 57-154114 | 9/1982 | Japan |
| 58-72102 | 4/1983 | Japan |
| 1483816 | 8/1977 | United Kingdom |
| 747850 | 7/1980 | U.S.S.R. |

Primary Examiner—A. Lionel Clingman
Attorney, Agent, or Firm—Oblon, Fisher, Spivak, McClelland & Maier

[57] ABSTRACT

A dental material having X-ray contrastability which is excellent in strength, aesthetic appearance, workability, marginal blocking and the like and possesses high value in use can be provided by using a methacrylate having an aromatic hydrocarbon substituted by bromine in the molecule as polymerizable monomer and, as occasion demands, combining a filler and/or hardener suitably selected with this compound.

7 Claims, No Drawings

DENTAL MATERIALS HAVING X-RAY CONTRASTABILITY

FIELD OF THE TECHNIQUE

This invention relates to a dental material having radiation contrastability and, in detail, it relates to a dental material having X-ray contrastability which comprises combining a methacrylate having an aromatic residue substituted by bromine atom in the molecule as polymerizable monomer.

BACKGROUND TECHNIQUES

As the materials for restoration in the field of dental cure such as restoration of a partially lost tooth and the like, plastic materials have been widely used in recent years. The plastic materials are excellnet in strength, aesthetic appearance, modability and economical efficiency and possesses almost properties required as the dental materials for restorative treatment. The plastic material, however, has X-ray permeability in itself and this property has been considered a disadvantage in practical use. Because, when inspections of dental caries, disorder of tissue and the like are required after dental cure, the observation by X-ray contrast is often conducted as a method to inspect the affected part undestructively, but, in this case, the detection of the affected part newly formed becomes difficult if the part to be cured is permeable. Therefore, as another property to be possessed by the dental materials for restorative treatment, X-ray impermeability has been considered important.

As methods to change the X-ray permeable materials to X-ray impermeable ones, the combination of powdery metals or the combination of oxides or salts of X-ray impermeable heavy metals, organic iodie compounds and the like are generally employed. These methods, however, have problems such as check of workability and modability of the plastic materials and deterioration of their water resisting property, transparency, light permeability, strength and the like, and also the fillers of the metals and the like mentioned above can not be combined in certain circumstances, and therefore, these methods could not give X-ray contrastability in fact for this purpose.

DISCLOSURE OF THE INVENTION

This invention is accomplished on the basis of these circumstances and aimes at providing a dental material having X-ray contrastability in which the above-mentioned disadvantages are improved by causing a bromine whch is a X-ray impermeable element to be present in a methacrylate by means of chemical bonding to endow the methacrylate itself which is a polymerizable monomer with X-ray contrastability.

Namely, this invention is characterized by employing a methacrylate which has one or more carbon-bromine bonds in the molecule as polymerizable monomer and, in more detail, it provides a dental material having X-ray contrastability which comprises combining a filler and/or hardener, as occasion demands, with a methacrylate which has a hydrocarbon residue having an aromatic residue substituted by bromine atom as component of the alcoholic side.

However, the too small content of bromine in the above-mentioned methacrylate can not afford a necessary and sufficient X-ray contrastability and, on the other hand, the too much gives a bad effect on the strength, aesthetic appearance or modability of the polymer, though it improves X-ray contrastability. Therefore, the preferable content of bromine atom occupied in the whole molecules of the methacrylate was examined and found to be in the range from 20 to 60 weight %. In this invention, the above methacrylate can also be used independently, but, preferably, it is advantageously used as a polymerizable composition by mixing with a reaction accelerator (e.g., amines) and a hardener (e.g., benzoyl peroxide, etc.) in order to control the reaction rate of the said polymerizable monomer or the hardness of the molding suitably and, moreover, various fillers (silica, quartz powder, metal powder, etc.) properly selected can be added in order to match the color of the said molding with the tooth or to increase the mechanical strength or X-ray contrastability of the molding.

As mentioned above, the greatest characteristic of this invention is to employ the methacrylate containing one or more carbon-bromine bonds in the molecule as polymerizable monomer, and this compound enables the materials for dental cure to be endowed with X-ray contrastability without injuring their required properties at all. Such methacrylates are illustrated in detail with more concrete examples.

The methacrylate used in this invention has a hydrocarbon residue having an aromatic residue substituted by bromine atom as component of the alcoholic side, and the aromatic residue substituted by the said bromine atom is bonded to the hydrocarbon residue through ether bonding, carboxylate bonding, pohsphate bonding and the like. The methacrylate is also particularly preferred to have one or two aromatic residues substituted by bromine in one molecule, and for those having two aromatic residues, the aromatic residues are bonded through a bivalent hydrocarbon.

Furthermore, the said methacrylate is used as a polymerizable monomer which hardens by three-dimentional cross linkage and thus it is required to have at least one or more methacrylic groups, preferably two or more methacrylic groups in the molecule, and particularly, it is recommended to have about two to four in general in view of synthetic reaction and the like.

In further concrete explannation about the methacrylate related to this invention, examples of those having two methacrylic groups in one molecule include the compound represented by the general formula (I).

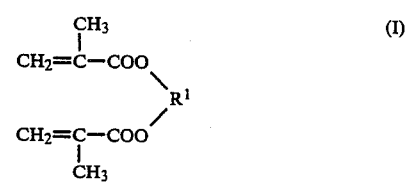

(I)

wherein $R^1$ represents a bivalent hydrocarbon residue which is discontinued by an aromatic residue substituted by bromine. Examples of those having four methacrylic groups in one molecule inclurde the compound represented by the general formula (II).

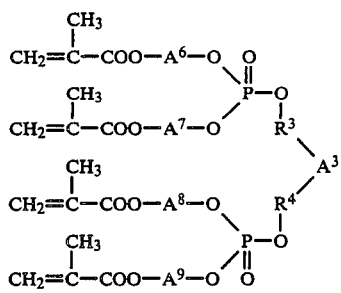
(II)

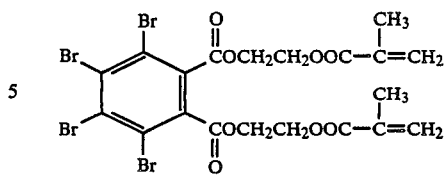
Compound I

Example of the latter:

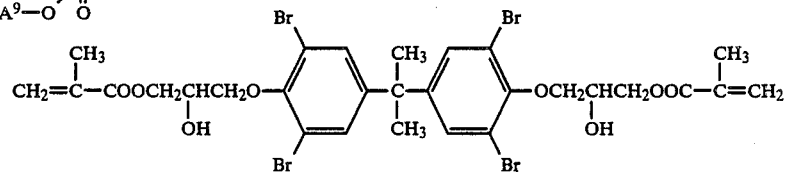
Compound II

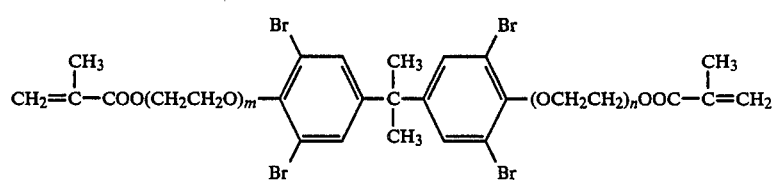
Compound III (m + n = 2~6)

On the other hand, the concrete examples of the compounds which afford preferable X-ray contrastability in the general formula (II) include;

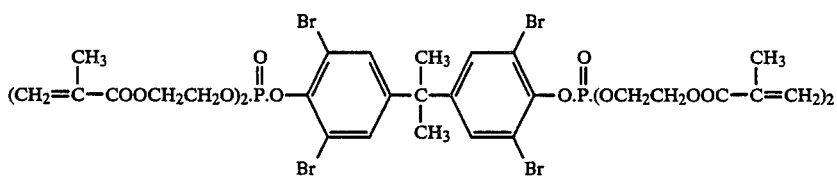
Compound IV wherein $A^6$, $A^7$, $A^8$, $A^9$ and $A^3$ each represents a bivalent hydrocarbon residue and $R^3$ and $R^4$, which are same or different, each represents a bivalent aromatic hydrocarbon residue substituted by bromine.

In the general formula (I), $R^1$ in the formula has the above-mentioned meaning, but examples of the particularly preferred groups include a hydrocarbon group having an aromatic residue substituted by bromine which is represented by $-A^1-OOC-R^2-COO-A^2-$ (wherein $R^2$ represents a bivalent aromatic residue substituted by bromine and $A^1$ and $A^2$ each represents a same or different bivalent hydrocarbon residue) or $-A^4-O-R^3-A^3-R^4-O-A^5-$ (wherein $A^3$ represents a bivalent hydrocarbon residue, $R^3$ and $R^4$, which are same or different, each represents a bivalent aromatic hydrocarbon residue substituted by bromine, $A^4$ and $A^5$, which are same or different, each represents a bivalent hydrocarbon residue which is discontinued by oxygen atom or not discontinued, and the said hydrocarbon residue may have a hydroxyl group as substituting part. Furthermore, among these compounds, the compounds which afford more preferable X-ray contrastability are concretely illustrated as follows.

Example of the former:

Hereinafter, this invention is further illustrated by Working Examples with respect to the dental materials having these methacrylates as basic component.

The infrared absorption spectrum analyses ($v_{cm}-1^{NEAT}$) of the said compounds in Working Examples mentioned below are carried out using Hitachi 270-30 Type Infrared Spectrophotometer after treatment of the compounds with active carbon in ethanol followed by decolorization.purification by column chromatography (alumina, a mixed solvent of acetate:n-hexane).

WORKING EXAMPLE 1

(Synthesis of Compound I)

A carbon tetrachloride solution containing dichloride tetrabromphthalate (519 g) was added dropwise to a carbon tetrachloride solution of 2-hydroxyethyl methacrylate (260 g) and pyridine (174 g) in a stream of $N_2$ under ice cooling. After the reaction was over, the reaction mixture was washed with 5% HCl, 5% NaOH and a saturated brine, the carbon tetrachloride solution was dried over sodium sulfate and then the solvent was removed to afford Compound I [Di-(2-methacryloxyethyl) tetrabromophthalate] (656 g, crude yield 93%).

IR: $v_{cm}-1^{NEAT}$; 2960, 2880, 1726, 1640, 1298, 1164, 656.

(Preparation of filling resin of ultrafine grain filler)

Colloidal silica (e.g., Aerozyl R 972 made by Japan Aerozyl Co.) 70 parts and benzoyl peroxide 3 parts which were homogeneously kneaded at 50°~60° C. was polymerized with trimethylolpropane trimethacrylate 30 weight parts by heating press. The resulting polymerized product was grinded using ball mill to prepare a filler having a grain size of 10 to 40 μm. This filler 200 weight parts, Compound I 50 weight parts, trimethylolpropane trimethacrylate 30 weight parts, bisphenol A.diglycidyl methacrylate 20 weight parts and tertiary buty hydroxytoluene 0.05 weight part were sufficiently mixed and kneaded to divide into two equal parts. Benzoyl peroxide 2.3 weight parts and N,N-diethanol-P-toluidine 2.0 weight parts were added to each part, respectively, to afford two kinds of pastes, A and B.

(Various tests)

The equivalents of the obtained pastes, A and B, were sufficiently kneaded, and hardening time and the compressive strength, diametral tensile strength or presence of X-ray contrastability of the hardened product were measured. The results are summarized in Table 1.

The measurements are carried out according to the following methods.

Hardening time: American Dental Association Specification No. 27 (Hardening time)

Compressive strength: A testing piece of 4×8 mmØ was prepared in a cylindrical golden mold, allowed to stand for 24 hours and then measured using Instrone operating at a cross delivery head rate of 1 mm/min.

Diametral tensile strength: American Dental Association Specification No. 27 (Diametral tensile strength)

X-ray contrastability: Dental X-ray consultation instrument (Sanekuseray Roentgen S-type: made by Sankin Kogyo Co.)

WORKING EXAMPLE 2

(Synthesis of Compound II)

To a carbon tetrachloride solution of tetrabromobisphenol A (544 g) and glycidyl methacrylate (313 g) were added 0.5% hydroquinone monomethylether and pyridine (174 g), and the reaction mixture was heated under reflux in a stream of nitrogen. After the reaction was over, the resulting mixture was washed with 5% HCl, 5% NaOH and a saturated brine, the carbon tetrachloride solution was dried over sodium sulfate and then the solvent was removed under reduced pressure to afford Compound II [Tetrabromobisphenol A diglycidyl methacrylate] (554 g, curde yield 67%).

IR: $v_{cm}^{-1 NEAT}$: 3450, 2950, 2880, 1720, 1635, 1450, 1295, 1270, 1150, 740, 656.

(Preparation of complexed filling resin)

Compound II 70 weight parts, diethyleneglycole dimethacrylate 30 weight parts, α-quartz powder having a grain size of 1 to 30 μm which was treated with silane 450 weight parts and tertiary butylhydroxytoluene 0.05 weight part were sufficiently mixed and kneaded to divide into two equal parts. Benzoyl peroxide 2.3 weight parts and N,N-diethanol-P-toluidine 20 weight parts were added to each parts, respectively, to afford two kinds of mixtures of paste type polymerized monomers, A and B.

(Various tests)

The equivalents of the obtained A and B were fully kneaded and subjected to the same tests as described in Working Example 1. The results are summarized in Table 1.

TABLE 1

|  | Hardening time | Compressive strength | Diametral tensile strength | X-ray contrastability |
| --- | --- | --- | --- | --- |
| Working Ex. 1 | 3' | 2,100 kg/cm² | 410 kg/cm² | excellent |
| Working Ex. 2 | 3'3" | 3,200 kg/cm² | 510 kg/cm² | excellent |

WORKING EXAMPLE 3

(Compound IV)

Tetrabromobisphenol A (544 g) and phosphorus oxychloride (383 g) were heated under reflux in the presence of calcium chloride (2 weights %). After the reaction was over, the excess phosphorus oxychloride was removed under reduced pressure to afford tetrabromobisphenol A disphophonyldichloride. Moreover, this compound was dissolved to carbon tetrachloride, and 2-hydroxyethyl methacrylate (572 g) and pyridine (348 g) were added dropwise thereto in a stream of N₂ at 0° to 5° C. After the addition was over, 0.5% hydroquinone was added to the reaction mixture and the mixture was heated under reflux in a stream of N₂. After the reaction was over, the resulting solution was washed with 5% HCl, 5% NaOH and a saturated brine and dried over sodium sulfate, and then the carbon tetrachloride was removed under reduced pressure to afford Compound IV [Tetrabromovisphenol A tetra(2-methacryloxyethyl)diphosphonate] (829 g, crude yield 72%).

IR: $v_{cm}^{-1 NEAT}$: 2950, 2880, 1720, 1630, 1600, 1365, 1295, 980, 656.

(Preparation of sealant)

Compound IV 70 weight parts, 2-hydroxyisopropyl methacrylate 30 weight parts, colloidal silica (Aerozyl R 972 made by Japan Aerozyl Co.) 1 weight part and tertiary butyl hydroxyltoluene 0.05 weight part were mixed sufficiently to divide into two equal parts. To one part were added benzoyl peroxide 3 weight parts and phenyl salicylate 2 weight parts and to the other was added N,N-diethyl-P-toluidine 2.5 weight parts, and two kinds of sealant solutions, A and B, were obtained.

(Various tests)

A lacuna of a fresh extracted tooth of man was edged with an aqueous solution of 40% phosphoric acid for 1 minute and filled by adding dropwise the mixed sealant solution of the above A and B. After allowed stand for 30 minutes, this testing piece was kept in water of 37° C. for 24 hours and then immersed in aqueous Fuchsine solutions of 4° C. and 60° C. alternately at intervals of 1 minute by 60 times to examine the degree of intrusion of pigment and evaluate the marginal blocking. The degree of intrusion of pigment was decided by cutting the extracted tooth which was immersed in the middle to examine the presence of intrusion of pigment between the tooth and the sealant. As a result, the intrusion of pigment was not recognized at all and the marginal blocking was excellent. The extracted tooth filled with the mixed sealant of the above A and B was subjected to X-ray contrastability test, and the filled material could be clearly distinguished from the tooth and thus the X-ray contrastability could be recognized.

AVAILABILITY IN INDUSTRIES

This invention is composed as describd above and relates to a dental material having X-ray contrastability which comprises combining a methacrylate having a X-ray impermeable bromine atom in the molecule as polymerizable monomer, and this compound enabled the said polymerizable complexed composition to be endowed with X-ray contrastability without reducing various properties such as strength, aesthetic appearance, modability and the like, and various public known fillers and hardeners to be combined as occasion demands, and also an excellent material for dental cure having X-ray contrastability to be provided even in the use where fillers can not be combined.

We claim:

1. A dental material having X-ray contrastability which comprises a polymerizable monomer having a bromine content of 20 to 60 wt percent and is of the formula

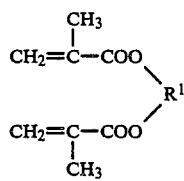
(I)

where $R^1$ is $-A^1-OOC-R^2-COO-A-A^2-$, wherein $R^2$ represents a bivalent aromatic residue substituted by bromine and $A^1$ and $A^2$ each represents a same or different bivalent hydrocarbon residue, or $-A^4-O-R^3-A^3-R^4-O-A^5-$, wherein $A^3$ represents a bivalent hydrocarbon residue, $R^3$ and $R^4$, which are same or different, each represents a bivalent aromatic hydrocarbon residue substituted by bromine, $A^4$ and $A^5$, which are same or different, each represent a bivalent hydrocarbon residue a bivalent residue consisting of hydrocarbon residues linked by oxygen, and the said hydrocarbon residues may have a hydroxyl group as a substituent.

2. A dental material according to claim 1 wherein the monomer is of the formula:

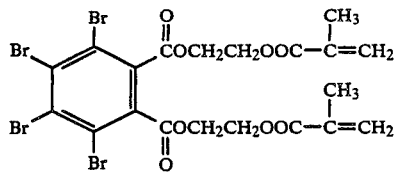

3. A dental material according to claim 1 wherein the polymerizable monomer is of the formula:

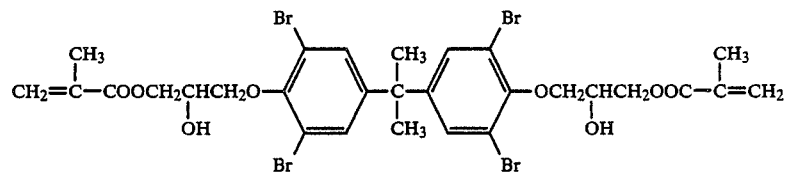

4. A dental material according to claim 1 wherein the polymerzable moomer is of the formula:

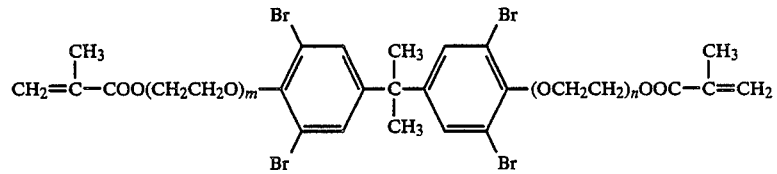

where m+n equals 2 to 6.

5. A dental material according to claim 1 which comprises an additional polymerizable methacrylate monomer having at leat two methacrylate groups other than the monomer of claim 1, which monomer imparts X-ray contrastability, a filler and a hardener.

6. A dental material according to claim 2 which comprises the monomer of claim 2, trimethylolpropane trimethacrylate, bisphenol A diglycidyl methacrylate, a filler, and a hardener.

7. A dental material according to claim 3 which comprises the monomer of claim 3 diethleneglycol dimethacrylate, a filler and a hardener.

* * * * *